US008901041B2

(12) United States Patent
Frisch et al.

(10) Patent No.: US 8,901,041 B2
(45) Date of Patent: Dec. 2, 2014

(54) LOW-FOAM AQUEOUS FORMULATIONS FOR CROP PROTECTION

(75) Inventors: Gerhard Frisch, Wehrheim (DE); Gerhard Schnabel, Elsenfeld (DE); Janine Rude, Kriftel (DE)

(73) Assignee: Bayer Intellectual Property GmbH, Monheim (DE)

( * ) Notice: Subject to any disclaimer, the term of this patent is extended or adjusted under 35 U.S.C. 154(b) by 1844 days.

(21) Appl. No.: 11/140,104

(22) Filed: May 27, 2005

(65) Prior Publication Data

US 2005/0266998 A1 Dec. 1, 2005

(30) Foreign Application Priority Data

Jun. 1, 2004 (DE) .................... 10 2004 026 938

(51) Int. Cl.
*A01N 57/20* (2006.01)
*A01N 25/30* (2006.01)
*A01N 25/22* (2006.01)

(52) U.S. Cl.
CPC .............. *A01N 25/30* (2013.01); *A01N 57/20* (2013.01); *A01N 25/22* (2013.01)
USPC ........................................ 504/362; 504/175

(58) Field of Classification Search
CPC ........ A01N 25/22; A01N 57/20; A01N 25/02
USPC ..................... 504/116.1, 362, 175
See application file for complete search history.

(56) References Cited

U.S. PATENT DOCUMENTS

| | | | |
|---|---|---|---|
| 3,799,758 A | 3/1974 | Franz et al. | |
| 4,400,196 A | 8/1983 | Albrecht et al. | |
| 4,714,479 A | 12/1987 | Wilsberg | |
| 5,332,714 A | 7/1994 | Albrecht et al. | |
| 5,491,125 A | 2/1996 | Albrecht et al. | |
| 5,525,578 A * | 6/1996 | Langeluddeke et al. | 504/128 |
| 6,566,308 B1 * | 5/2003 | Aven | 504/347 |
| 2002/0055436 A1 * | 5/2002 | Krause et al. | 504/118 |
| 2005/0164884 A1 | 7/2005 | Bramati et al. | |

FOREIGN PATENT DOCUMENTS

| | | |
|---|---|---|
| DE | 3427078 | 1/1986 |
| EP | 0 048 436 A1 | 3/1982 |
| EP | 0 336 151 A2 | 10/1989 |
| EP | 0 402 769 | 12/1990 |
| EP | 1 093 722 A2 | 1/1991 |
| EP | 0 413 267 A1 | 2/1991 |
| EP | 0 407 871 A1 | 11/1992 |
| WO | WO 95/00017 | 1/1995 |
| WO | WO 00/08925 | 2/2000 |
| WO | WO 03/065803 A2 | 8/2003 |
| WO | WO 2005/054370 A2 | 6/2005 |

* cited by examiner

*Primary Examiner* — Johann R. Richter
*Assistant Examiner* — Danielle Sullivan
(74) *Attorney, Agent, or Firm* — Frommer Lawrence & Haug LLP

(57) ABSTRACT

Liquid aqueous formulations of water-soluble active crop protectant ingredients which comprise
(a) one or more water-soluble active ingredients (type (a) ingredients),
(b) if desired, one or more water-insoluble active ingredients (type (b) ingredients),
(c) if desired, polar organic solvents,
(d) anionic surfactants,
(e) if desired, nonionic, cationic and/or zwitterioinic surfactants,
(f) silicone-based defoamers from the group of the linear polydimethylsiloxanes having an average dynamic viscosity, measured at 25° C., in the range from 1000 to 8000 mPas, and containing silica,
(g) if desired, other, customary formulation assistants, and
(h) water are suitable as low-foam formulations for application in crop protection.

Also possible is the use of the corresponding active-ingredient-free adjuvant formulations in a tank mix with or in split application with active-ingredient formulations.

17 Claims, No Drawings

LOW-FOAM AQUEOUS FORMULATIONS FOR CROP PROTECTION

The invention relates to the technical field of preparations (formulations) for active ingredients in the plant protection field (agrochemical active ingredients), preferably aqueous formulations of water-soluble active crop protectant ingredients, in particular aqueous formulations of saltlike active crop protectant ingredients, and especially glufosinate-ammonium. The invention also relates to mixtures of adjuvants which can be used in combination with the stated active crop protectant ingredients and formulations thereof.

Aqueous formulations of glufosinate-ammonium are known, for example, from EP-A-0048436, EP-A-00336151, and EP-A-1093722. Because of the surfactants that are present in the formulations and boost the activity, the formulations exhibit unfavorable foam behavior when diluted with water prior to application, and during spraying in the course of application, unless defoamers are added. The consequences then are often overflow of spray apparatus, contamination of the environment, uneven spray deposits on the crops, and crop protectant residues in the spray apparatus.

For aqueous liquid crop protectant compositions, EP-A-0407874 proposed effective defoamers from the group of the perfluoroalkylphosphinic or -phosphonic acids. Defoamers of this kind (e.g., ®Fluowet PP from Clariant) are distinguished by a combination of high defoamer activity and comparatively low application rate, the defoamer activity remaining stable even on prolonged storage at different temperatures and in the event of mechanical stress acting on the formulations. Furthermore, the biological activity of the formulated crop protectant compositions is unaffected by the defoamer content.

The known fluorinated defoamers, however, are not equally suitable for all fields of application. In the case of many such formulations, for example, the defoaming activity is dependent on the hardness of the water (the calcium and magnesium salt content) used to prepare the spray liquors. From general ecotoxicological considerations as well, whereby the amount of fluorinated hydrocarbons in the environment is to be reduced, there is a need for alternative defoamers which allow the preparation of low-foam formulations of active crop protectant ingredients with good performance properties: for example, good stability on storage and high, uniform biological activity.

Silicone-based defoamers are likewise among known highly active defoamers. In some cases, however, they have performance disadvantages, which cause them to appear less suitable for use for formulations of aqueous solutions of polar crop protectant ingredients, especially saltlike ingredients such as glufosinate-ammonium. Thus some defoamers are poorly soluble in the aqueous formulations and deposit in the form of cloudiness, flocculation or phase separation. Other defoamers of this kind no longer exhibit a sufficient defoamer activity after the formulations being stored at room temperature or at an elevated temperature with up to 50° C., for example.

The aforementioned EP-A-0407874 mentions numerous examples of known, silicone-based defoamers, but these have few or no useful qualities as defoamers for aqueous crop protectant compositions of saltlike active ingredients.

In addition, replacing the defoamers in many known crop protectant compositions by other defoamers is found from experience, and in accordance with our own experiments, to lead in many cases to a marked reduction in the biological activity of the formulations.

The object is therefore to provide defoamers for aqueous formulations of saltlike water-soluble crop protectants that eliminate or reduce the aforementioned disadvantages and can be used with one or more advantages.

Surprisingly it has now been found that various silicone-based defoamers unexpectedly exhibit good performance properties in the abovementioned formulations of saltlike active crop protectant ingredients, and in particular not only provide effective defoaming but also result in formulations which exhibit a comparatively high biological activity when used as intended.

The invention accordingly provides liquid aqueous crop protectant compositions of water-soluble active crop protectant ingredients, said compositions comprising
(a) one or more water-soluble active crop protectant ingredients (type (a) active ingredients),
(b) if desired, one or more water-insoluble active crop protectant ingredients (type (b) active ingredients),
(c) if desired, polar organic solvents,
(d) anionic surfactants,
(e) if desired, nonionic, cationic and/or zwitterionic surfactants,
(f) silicone-based defoamers from the group of the linear polydimethylsiloxanes having an average dynamic viscosity, measured at 25° C., in the range from 1000 to 8000 mPas, and containing silica,
(g) if desired, other customary formulation assistants, and
(h) water.

The aqueous formulations of the invention, containing defoamer, are suitable preferably for type (a) active ingredients from the group of the salt-containing water-soluble active ingredients such as glufosinate (salts), glyphosate (salts), paraquat, diquat and the like, especially glufosinate-ammonium.

The formulations of the invention may further comprise type (b) active ingredients, which are largely insoluble in water, examples being herbicides from the group of the diphenyl ethers such as oxyfluorfen, carbamates, thiocarbamates, triphenyltin compounds and tributyltin compounds, haloacetanilides, phenoxyphenoxyalkanecarboxylic acid derivatives and heteroaryloxyphenoxyalkanecarboxylic acid derivatives, such as quinolyloxy-, quinoxalyloxy-, pyridyloxy-, benzoxalyloxy- and benzothiazolyloxyphenoxyalkanecarboxylic esters, examples being diclofop-methyl, fenoxaprop-ethyl, and fenoxaprop-P-ethyl.

Also suitable are correspondingly insoluble active ingredients from classes of substance which normally include active ingredients of different solubilities, examples being active ingredients from the group of the cyclohexanedione derivatives, imidazolinones, pyrimidyloxypyridinecarboxylic acid derivatives, pyrimidyloxybenzoic acid derivatives, sulfonylureas, triazolopyrimidinesulfonamide derivatives, and S—(N-aryl-N-alkylcarbamoylmethyl)dithiophosphoric esters.

The stated common names for active ingredients, such as glufosinate, glyphosate, oxyfluorfen, diclofop-methyl, fenoxaprop-(P-)ethyl and others, are known to the skilled worker; see, for example, "The Pesticide Manual" British Crop Protection Council 2003; the names include the known derivatives such as salts of glufosinate and glyphosate, especially the commercially customary forms.

Correspondingly it is also possible for active ingredients from the group of the safeners, growth regulators, insecticides and fungicides to be suitable as component (b) and/or, given good water-solubility, as components (a).

The type of active ingredients (a) and (b) used determine the type of pests which can be controlled by application of the crop protection compositions or agrochemical formulations. In case of herbicides the pests are undesired plants.

Preferred formulations are those comprising type (a) ingredients from the group consisting of one or more compounds of the formula (1) or salts thereof,

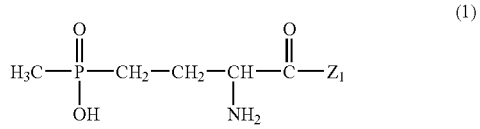

(1)

in which
Z$_1$ is a radical of the formula —OM, —NHCH(CH$_3$)CON-HCH(CH$_3$)CO$_2$M or —NHCH(CH$_3$)CONHCH [CH$_2$CH(CH$_3$)$_2$]CO$_2$M where
M=H or a salt-forming cation,
and/or one or more compounds of the formula (2) or salts thereof,

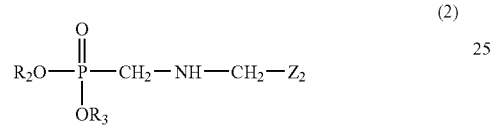

(2)

in which
Z$_2$ is a radical of the formula CN or CO$_2$R$_1$, in which R$_1$=Q or a salt-forming cation and Q=H, alkyl, alkenyl, alkoxyalkyl or C$_6$-C$_{10}$-aryl which is unsubstituted or substituted and is preferably unsubstituted or substituted by one or more radicals from the group consisting of alkyl, alkoxy, halogen, CF$_3$, NO$_2$ and CN, and
R$_2$ and R$_3$ each independently of one another are H, alkyl, C$_6$-C$_{10}$-aryl which is unsubstituted or substituted and is preferably unsubstituted or substituted by one or more radicals from the group consisting of alkyl, alkoxy, halogen, CF$_3$, NO$_2$ and CN, or are biphenylyl or a salt-forming cation.

Preferably, the carbon-containing radicals in connection with Q, R$_2$ or R$_3$, respectively have up to 10 carbon atoms, particularly preferred up to 6 carbon atoms.

The compounds of the formula (1) include an asymmetric carbon atom. The L enantiomer is regarded as the biologically active isomer. The formula (1) hence embraces all stereoisomers and mixtures thereof, particularly the racemate, and the biologically active enantiomer in each case. Examples of active ingredients of the formula (1) are as follows:

glufosinate and its ammonium salt in racemic form, i.e., 2-amino-4-[hydroxy(methyl)phosphinoyl]butanoic acid and its ammonium salt, the L enantiomer of glufosinate and its ammonium salt,
bilanafos/bialaphos, i.e., L-2-amino-4-[hydroxy(methyl) phosphinoyl]butanoyl-L-alaninyl-L-alanine and its sodium salt.

The racemate of glufosinate-ammonium is on its own delivered usually at doses of between 200 and 1000 g a.i./ha (i.e., grams of active ingredient per hectare). These doses, glufosinate-ammonium is particularly effective when it is taken up by green parts of the plants; see "The Pesticide Manual" 13th Edition, British Crop Protection Council 2003. Glufosinate-ammonium is used predominantly for controlling broadleaf and gramineous weeds in plantation crops and on uncultivated land and also, using special application techniques, for inter-row control in arable crops such as corn, cotton, etc. Its use is also of increasing significance in transgenic crops which are tolerant or resistant to the active ingredient.

The compounds of the formula (2) comprise N-(phosphonoalkyl)glycine and hence derivatives of the amino acid glycine. The herbicidal properties of N-(phosphonomethyl)glycine (glyphosate) are described for example in U.S. Pat. No. 3,799,758.

In crop protection formulations, glyphosate is used generally in the form of the water-soluble salts, the isopropylammonium salt in particular being of importance in connection with the present invention; see "The Pesticide Manual" 13th Edition, British Crop Protection Council 2003.

In connection with the present invention the term "polar organic solvents" (component (c)) refers for example to polar protic or aprotic polar solvents and mixtures thereof. Examples of solvents in the sense of the invention are aliphatic alcohols, such as lower alkanols such as methanol, ethanol, propanol, isopropanol and butanol, or polyhydric alcohols such as ethylene glycol and glycerol, for example, polar ethers such as tetrahydrofuran (THF), dioxane, alkylene glycol monoalkyl and dialkyl ethers, such as propylene glycol monomethyl ether, propylene glycol monoethyl ether, ethylene glycol monomethyl or monoethyl ether, diglyme and tetraglyme, for example;

amides such as dimethylformamide (DMF), dimethylacetamide, dimethylcaprylamide, dimethylcapramide (®Hallcomide) and N-alkylpyrrolidones;

ketones such as acetone;

esters based on glycerol and carboxylic acids, such as glyceryl mono-, di- and triacetate, lactams;

carbonic diesters;

nitriles such as acetonitrile, propionitrile, butyronitrile and benzonitrile;

sulfoxides and sulfones such as dimethyl sulfoxide (DMSO) and sulfolane.

Also suitable in many cases are combinations of different solvents which additionally include alcohols such as methanol, ethanol, n- and isopropanol, n-, iso-, tert- and 2-butanol.

In the case of single-phase aqueous-organic solutions the wholly or largely water-miscible solvents or solvent mixtures are appropriate.

Preferred organic solvents in the sense of the present invention are polar organic solvents such as N-methylpyrrolidone and Dowanol® PM (propylene glycol monomethyl ether).

Formulations of the invention comprise as component (d) anionic surface-active compounds (anionic surfactants). Examples of anionic surfactants (where EO=ethylene oxide units, PO=propylene oxide units and BO=butylene oxide units) are:

d1) anionic derivatives of fatty alcohols having 10-24 carbon atoms with 0-60 EO and/or 0-20 PO and/or 0-15 BO in any order, in the form of ether carboxylates, sulfonates, sulfates and phosphates and their inorganic (e.g., alkali metal and alkaline earth metal) and organic salts (e.g., those based on amine or alkanolamine), such as Genapol® LRO, Sandopan® grades, Hostaphat/ Hordaphos® grades from Clariant;

d2) anionic derivatives of copolymers composed of EO, PO and/or BO units with a molecular weight of 400 to 10$^8$, in the form of ether carboxylates, sulfonates, sulfates and phosphates and their inorganic (e.g., alkali metal and alkaline earth metal) and organic salts (e.g., those based on amine or alkanolamine);

d3) anionic derivatives of alkylene oxide adducts of $C_1$-$C_9$ alcohols, in the form of ether carboxylates, sulfonates, sulfates and phosphates and their inorganic (e.g., alkali metal and alkaline earth metal) and organic salts (e.g., those based on amine or alkanolamine);

d4) anionic derivatives of fatty acid alkoxylates in the form of ether carboxylates, sulfonates, sulfates and phosphates and their inorganic (e.g., alkali metal and alkaline earth metal) and organic salts (e.g., those based on amine or alkanolamine);

d5) salts of aliphatic, cycloaliphatic and olefinic carboxylic and polycarboxylic acids, and also alpha-sulfo fatty acid esters as are obtainable from Henkel;

d6) sulfosuccinates, alkanesulfonates, paraffinsulfonates and olefinsulfonates such as Netzer IS®, Hoe®S1728, Hostapur®OS, Hostapur®SAS from Clariant, Triton®GR₇ME and GR₅ from Union Carbide, Empimin® grades from Albright and Wilson, and Marion®-PS65 from Condea.

Preferred anionic surfactants are alkyl polyglycol ether sulfates, especially fatty alcohol diethylene glycol ether sulfate (e.g., Genapol LRO®, Clariant), or alkyl polyglycol ether carboxylates (e.g., 2-(isotridecyloxypolyethyleneoxy)ethyl carboxymethyl ether, Marlowet 4538®, Hüls).

The formulations of the invention may if desired comprise nonionic and/or cationic surfactants as component (e).

Examples of nonionic surfactants (for surfactant component e) are:

e1) fatty alcohols having 10-24 carbon atoms with 0-60 EO and/or 0-20 PO and/or 0-15 BO in any order. Examples of such compounds are Genapol® C, L, O, T, UD, UDD and X grades from Clariant, Plurafac® and Lutensol® A, AT, ON and TO grades from BASF, Marlipal® 24 and O13 grades from Condea, Dehypon® grades from Henkel, and Ethylan® grades from Akzo-Nobel such as Ethylan DC 120;

e2) fatty acid alkoxylates and triglyceride alkoxylates such as the Serdox® NOG grades from Condea or the Emulsogen® grades from Clariant;

e3) fatty acid amide alkoxylates such as the Comperlan® grades from Henkel or the Amam® grades from Rhodia;

e4) alkylene oxide adducts of alkynediols such as the Surfynol® grades from Air Products; sugar derivatives such as amino sugars and amido sugars from Clariant, e5) glucitols from Clariant, e6) alkylpolyglycosides in the form of the APG® grades from Henkel;

e7) sorbitan esters in the form of the Span® or Tween® grades from Uniqema;

e8) cyclodextrin esters or ethers from Wacker;

e9) surface-active cellulose derivatives and algine, pectin and guar derivatives such as the Tylose® grades from Clariant, the Manutex® grades from Kelco, and guar derivatives from Cesalpina;

e10) polyol-based alkylene oxide adducts such as Polyglykol® grades from Clariant;

e11) surface-active polyglycerides and their derivatives from Clariant.

Examples of cationic surfactants (for surfactant component e) are alkylene oxide adducts of fatty amines and corresponding quaternary ammonium compounds having 8 to 22 carbon atoms such as, for example, the Genamin® C, L, O and T grades from Clariant.

Also possible if desired are surface-active zwitterionic compounds such as taurides, betaines and sulfobetaines in the form of Tegotain® grades from Goldschmidt and Hostapon®T and Arkopon®T grades from Clariant (for surfactant component e).

The formulations of the invention comprise defoamers of component (f), which represent defoamers from the group consisting of linear polydimethylsiloxanes which have an average dynamic viscosity, measured at 25° C., in the range from 1000 to 8000 mPas (mPas=millipascal-second), preferably 1200 to 6000 mPas, and contains silica. By silica is meant, for example, forms/modifications such as polysilicic acids, meta-silicic acid, ortho-silicic acid, silica gel, silicic acid gels, kieselguhr, precipitated $SiO_2$ etc.

Defoamers from the group of the linear polydimethylsiloxanes include as their chemical backbone a compound of the formula HO—[Si(CH$_3$)$_2$—O—]$_n$—H, in which the end groups are modified—etherified, for example—or, in general, are joined to the groups —Si(CH$_3$)$_3$.

The amount of silica can be modified within a wide range and is generally in the range from 0.1 to 10 percent by weight, preferably 0.2 to 5 percent by weight, in particular 0.2% to 2% by weight of silica, based on the weight of polydimethylsiloxane.

Examples of defoamers of this kind are ®Rhodorsil Antifoam 416 (Rhodia) and ®Rhodorsil Antifoam 481 (Rhodia).

®Rhodorsil Antifoam 416 is a medium-viscosity silicone oil having a dynamic viscosity at 25° C. of about 1500 mPas and containing a surfactant and silica. Because of the surfactant content the density is reduced as compared with the unadditized silicone oil, and amounts to about 0.995 g/cm$^3$.

®Rhodorsil Antifoam 481 is a medium-viscosity silicone oil having a dynamic viscosity at 25° C. of about 4500 mPas and containing silica. The density amounts to about 1.045 g/cm$^3$.

The silicone oils can also be used as emulsions.

Preference is given to the use of medium-viscosity defoamers based on polydimethylsiloxanes having a dynamic viscosity, measured at 25° C., in the range from 2000 to 5000 mPas, preferably 4000 to 5000 mPas, and containing silica, in particular ®Rhodorsil Antifoam 481.

Examples of customary formulation assistants (g) are inert materials, such as stickers, wetters, dispersants, emulsifiers, penetrants, preservatives, and frost protectants, fillers, carriers and colorants, evaporation inhibitors and pH modifiers (buffers, acids and bases) or viscosity modifiers (e.g., thickeners).

The assistants needed to prepare the above formulations, such as surfactants in particular, are known in principle and are described for example in: McCutcheon's "Detergents and Emulsifiers Annual", MC Publ. Corp., Ridgewood N.J.; Sisley and Wood "Encyclopedia of Surface Active Agents", Chem. Publ. Co. Inc., New York 1964; Schönfeldt, "Grenzflächenaktive Äthylenoxidaddukte", Wiss. Verlagsgesellschaft, Stuttgart 1976; Winnacker-Küchler, "Chemische Technologie", Volume 7, C. Hanser-Verlag, Munich, 4th Edition 1986, and references cited in each of these.

With the aid of mixtures of components it is possible accordingly to prepare preferably concentrated low-foam liquid aqueous preparations of saltlike active crop protectant ingredients, such as glufosinate-ammonium, which comprise (a) 1% to 40%, preferably 2% to 30% and in particular 5% to 20% by weight of water-soluble active crop protectant ingredients (type (a) ingredients), (b) 0 to 40%, preferably 0 to 20% and in particular 0 to 10% by weight of water-insoluble active crop protectant ingredients (type (b) ingredients), (c) 0% to 50%, preferably 0 to 30% and in particular 0 to 20% by weight of polar organic solvents, (d) 1% to 80%, preferably 5% to 70% and in particular 6% to 60% by weight of anionic surfactants, (e) 0 to 20%, preferably 0 to 15%, by weight of nonionic, cationic and/or zwitterionic surfactants, (f) 0.02% to 10%, preferably 0.05% to 5% and in particular 0.1% to 2% by weight of the silica-containing defoamer for use in accordance with the invention, (g) 0 to 30%, preferably 0 to 20% and preferably 0 to 15% by weight of customary formulation assistants, (h) 0.1% to 90%, preferably 5% to 85%, by weight of water, more preferably 10% to 60% of water.

The weight ratio of the active ingredients (a), e.g. herbicides (a), to the anionic surfactants specified under (d), based in each case on the respective detersive ingredient (DTI), is generally in the range from 1:0.1 to 1:10, in particular 1:0.2 to 1:8, especially 1:0.2 to 1:5.

The weight ratio of the active ingredients (a), herbicides (a), to the defoamers specified under (f) is generally in the range from 1000:1 to 1:1, preferably 500:1 to 3:1, in particular 100:1 to 5:1.

The weight ratio of the anionic surfactants (d) to the defoamers specified under (f) is generally in the range from 2000:1 to 1:1, preferably 1000:1 to 5:1, in particular 500:1 to 10:1.

Further preference is also given to aqueous solutions, preferably single-phase solutions, which comprise (a) 1% to 40%, preferably 2% to 30% and in particular 5% to 20% by weight of water-soluble active ingredients of the stated type (a), preferably glufosinate-ammonium, (c) 0% to 40%, preferably 0 to 30% and in particular 0 to 20% by weight of polar organic solvents, (d) 3% to 80%, preferably 5% to 70% and in particular 6% to 60% by weight of anionic surfactants, (e) 0 to 20%, preferably 0 to 15%, by weight of nonionic, cationic and/or zwitterionic surfactants, (f) 0.02% to 10%, preferably 0.05% to 5% and in particular 0.1% to 2% by weight of the silica-containing defoamer for use in accordance with the invention, (g) 0 to 30%, preferably 0 to 20% and preferably 0 to 15% by weight of customary formulation assistants, (h) 0.1% to 90%, preferably 5% to 85%, by weight of water, more preferably 10% to 60% of water.

The solvents which can be admixed for the purpose of preparing the aqueous single-phase solution are in particular organic solvents of unlimited or substantial miscibility with water, such as N-methylpyrrolidone (NMP), dimethylformamide (DMF), dimethylacetamide (DMA) or Dowanol® PM (propylene glycol monomethyl ether), for example.

Examples of customary formulation assistants (g) are the specified inert materials, frost protectants, evaporation inhibitors, preservatives, colorants, etc.; preferred formulation assistants (g) are frost protectants and evaporation inhibitors such as glycerol or ethylene glycol, in an amount of 2% to 10% by weight, for example, and preservatives, e.g., Mergal K9N® (Riedel) or Cobate C®.

Additionally the formulations may comprise, as customary formulation assistants (g), defoamers of a different kind than those of component (f).

The liquid formulations of the invention can be prepared by methods which are customary in principle, i.e., by mixing the components with stirring or shaking or by means of static mixing methods. The liquid formulations obtained are stable with good storage properties.

The invention further provides low-foam liquid adjuvant formulations which can be used for preparing the stated concentrated crop protectant formulations or for preparing tank mixes with active crop protectant ingredient formulations, or else may be applied separately, simultaneously or sequentially with the application of active ingredients (preferably the stated active ingredients (a)) to the plants or to the soil on or in which the plants are growing.

Adjuvant formulations of this kind comprise (c) if desired, polar organic solvents, (d) anionic surfactants, (e) if desired, nonionic, cationic and/or zwitterionic surfactants, (f) silicone-based defoamers from the group of the linear polydimethylsiloxanes having an average dynamic viscosity, measured at 25° C., in the range from 1000 to 8000 mPas and containing silica, (g) if desired, other customary formulation assistants, and (h) water, components (c), (d), (e), (f), (g) and (h) being as defined for the aforementioned crop protectant formulations comprising active ingredient.

Preferred liquid adjuvant formulations comprise (c) 0% to 60%, preferably 0 to 40% and in particular 0 to 30% by weight of polar organic solvents, (d) 3% to 85%, preferably 6% to 80% and in particular 8% to 70% by weight of anionic surfactants, (e) 0 to 25%, preferably 0 to 20%, by weight of nonionic, cationic and/or zwitterionic surfactants, (f) 0.02% to 15%, preferably 0.05% to 10% and in particular 0.1% to 5% by weight of the silica-containing defoamer for use in accordance with the invention, (g) 0 to 40%, preferably 0 to 30% and preferably 0 to 20% by weight of customary formulation assistants, (h) 0.1% to 95%, preferably 5% to 90%, by weight of water, more preferably 10% to 70% of water.

The liquid formulations comprising active ingredient and the adjuvant formulations are low-foam formulations with good storage properties. In many cases they have very favorable technical properties on application. By way of example the formulations are distinguished by a low tendency to foam when diluted with water, as for example when preparing tank mixes or when the formulations are applied by spraying. The formulations with active ingredient and the adjuvant formulations, when employed together with active ingredients/active ingredient formulations, also display a very good biological action by comparison with formulations prepared using other silicone-based defoamers.

Accordingly the formulations of the invention are especially suitable for use in crop protection where the formulations are applied to the plants, to parts of plants or to the area under cultivation.

In the case of herbicidal ingredients (a) and/or (b) the formulations are very suitable for controlling unwanted plant growth both on uncultivated land and in tolerant crops.

In the examples below, quantities are by weight, unless indicated otherwise. The examples of Tables 1 and 2 relate to inventive stable compositions. Table 3 specifies comparative formulations. Tables 4 and 5 contain results of defoaming tests.

TABLE 1

Formulations (inventive)

| | 1 [1] | 2 | 3 | 4 | 5 | 6 | 7 | 8 |
|---|---|---|---|---|---|---|---|---|
| Glufosinate-ammonium (a.i.) | 18.00 | 18.00 | 14.00 | 14.00 | 12.00 | 12.00 | 6.00 | 6.00 |
| $C_{12}/C_{14}$—O-$(EO)_2$—$SO_3^-Na^+$ [2] | 21.00 | 21.00 | 42.00 | 42.00 | 12.60 | 12.60 | 6.30 | 6.30 |
| Propylene glycol monomethyl ether | 10.00 | 10.00 | 10.00 | 10.00 | 10.00 | 10.00 | — | — |
| Rhodorsil 481 [3] | 0.25 | 0.50 | 0.25 | 0.50 | 0.25 | 0.50 | 0.25 | 0.50 |
| Water [5] | ad 100 | ad 100 | ad 100 | ad 100 | ad 100 | ad 100 | ad 100 | ad 100 |

Abbreviations in Table 1: see after Table 3

TABLE 2

Formulations (inventive)

| | 9 [1] | 10 | 11 | 12 | 13 | 14 | 15 | 16 |
|---|---|---|---|---|---|---|---|---|
| Glufosinate-ammonium (a.i.) | 18.00 | 18.00 | 14.00 | 14.00 | 12.00 | 12.00 | 6.00 | 6.00 |
| $C_{12}/C_{14}$—O-$(EO)_2$—$SO_3^-Na^+$ [2] | 21.00 | 21.00 | 42.00 | 42.00 | 12.60 | 12.60 | 6.30 | 6.30 |
| Propylene glycol monomethyl ether | 10.00 | 10.00 | 10.00 | 10.00 | 10.00 | 10.00 | — | — |
| Rhodorsil 416 [4] | 0.25 | 0.50 | 0.25 | 0.50 | 0.25 | 0.50 | 0.25 | 0.50 |
| Water (ad 100%) [5] | ad 100 | ad 100 | ad 100 | ad 100 | ad 100 | ad 100 | ad 100 | ad 100 |

Abbreviations in Table 2: see after Table 3

TABLE 3

Comparative formulations

| | 17 [1] | 18 | 19 | 20 | 21 | 22 |
|---|---|---|---|---|---|---|
| Glufosinate-ammonium (a.i.) | 18.00 | 18.00 | 18.00 | 14.00 | 14.00 | 14.00 |
| $C_{12}/C_{14}$—O-$(EO)_2$—$SO_3^-Na^+$ [2] | 21.00 | 21.00 | 21.00 | 42.00 | 42.00 | 42.00 |
| Propylene glycol monomethyl ether | 10.00 | 10.00 | 10.00 | 10.00 | 10.00 | 10.00 |
| Antifoam SE 39 [6] | 0.50 | | | 0.50 | | |
| Antimussol 4459-2 [7] | | 0.50 | | | 0.50 | |
| Rhodorsil 1824 [8] | | | 0.50 | | | 0.50 |
| Water (ad 100%) [5] | ad 100 | ad 100 | ad 100 | ad 100 | ad 100 | ad 100 |

Abbreviations in Tables 1 to 3:
a.i. amount based on active ingredient
[1] the columns list the compositions of formulations 1 to 8 (in Table 1) or 9 to 16 (in Table 2) or 17 to 22 (in Table 3), respectively, with each line containing the amount of the component identified in the first column, in percent by weight;
[2] $C_{12}/C_{14}$ fatty alcohol diethylene glycol ether sulfate, amount of surfactant based on DTI="detersive ingredient", (used in the form of ®Genapol LRO, Clariant)
[3] ®Rhodorsil 481 (polydimethylsiloxane with silica gel, Rhodia)
[4] ®Rhodorsil 416 (polydimethylsiloxane with silica gel and surfactant, Rhodia)
[5] the amount of water is indicated as ad 100% and also includes small amounts of nonaqueous coconstituents that may be present in certain components employed, such as colorants, preservatives, etc.
[6] Antifoam EM SE 39 (silicone-based defoamer emulsion without silica gel, Wacker)
[7] ®Antimussol 4459-2 (silicone-based defoamer emulsion without silica gel, Clariant)
[8] ®Rhodorsil 1824 (silicone-based defoamer emulsion without silica gel, Rhodia)

Foam Test 1
The concentrated liquid crop protection formulation was diluted with the stated concentration to a 1% strength solution, with stirring, and the foam formed was measured after 10 seconds and 30 minutes as a percentage of the amount introduced (CIPAC standard). Some results are compiled in Table 4.

TABLE 4

(for foam test 1)

| | Formulation No. [1] | | | | | | | | |
|---|---|---|---|---|---|---|---|---|---|
| Foam test [2] | 1 | 3 | 5 | 8 | 17 | 18 | 19 | 20 | 21 | 22 |
| Foam (in %) after 10 sec for a 1% strength solution | 37 | 44 | 40 | 28 | 28 | 50 | 44 | 30 | 52 | 28 |
| Foam (in %) after 30 min for a 1% strength solution | 1 | 0 | 2 | 0 | 12 | 30 | 28 | 28 | 48 | 20 |

Abbreviations in Table 4:
[1] the formulations are numbered as per Tables 1 to 3
[2] foam according to CIPAC standard Foam Test 2
The respective concentrated liquid crop protection formulation was diluted with 30 times the amount of water in a spray tank (RAU sprayer, 400 l capacity). The foam behavior was measured as a percentage based on the volume of the amount introduced, after defined intervals of time with stirring or standing. As the experiments show, the inventive formulations of Tables 1 and 2 exhibit advantageous foam behavior.

In addition there are no instances of unwanted precipitation or flocculation of the nonaqueous components. Some experimental results are compiled in Table 5.

TABLE 5

(for foam test 2)

| Formulation[1] | Foam after introduction | Foam after 5 min stirring | Foam after 5 min standing |
|---|---|---|---|
| Formulation No. 1 | 10% | 5% | 0% |
| Formulation No. 3 | 10% | 3% | 3% |
| Formulation No. 5 | 10% | 4% | 2% |
| Formulation No. 8 | 12% | 5% | 5% |

Formulations in Table 5:
[1] the formulations are numbered as per Tables 1 to 3

BIOLOGICAL EXAMPLES

The formulations of Tables 1 and 2 were diluted with water as indicated in the above foam test and applied at a water application rate of 200 l/ha to uncultivated land containing a weed plant spectrum that had emerged under natural conditions. Evaluation after 4 weeks indicated that the green parts of the weed plants had died off and hence that effective weed plant control had been achieved.

What is claimed is:
1. A liquid aqueous herbicidal composition consisting of:
(a) 1% to 40% by weight of one or more water-soluble herbicidal active ingredients selected from the group consisting of compounds of the formula (1) or salts thereof:

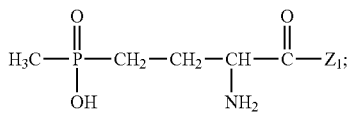

(1)

in which $Z_1$ is a radical of the formula:

—OM;

—NHCH(CH$_3$)CONHCH(CH$_3$)CO$_2$M; or

—NHCH(CH$_3$)CONHCH[CH$_2$CH(CH$_3$)$_2$]CO$_2$M;

where:
M=H or a salt-forming cation;
(c) 0% to 50% by weight of polar organic solvents;
(d) 1% to 80% by weight of anionic surfactants;
(e) 0 to 20% by weight of nonionic, cationic, and/or zwitterionic surfactants;
(f) 0.02% to 10% by weight of silicone-based defoamers selected from the group of the linear polydimethylsiloxanes having an average dynamic viscosity, measured at 25° C., in the range from 1000 to 8000 mPas, and containing silica;
(g) 0 to 30% by weight of other customary formulation assistants; and
(h) 0.1% to 90% by weight of water.
2. The herbicidal composition as claimed in claim 1;
wherein component (c) is present in an amount of 0% to 40% by weight;
wherein component (d) is present in an amount of 3% to 80% by weight;
wherein component (f) contains 0.1 to 10% by weight of silica based on the weight of polydimethylsiloxane.
3. The herbicidal composition as claimed in claim 1;
wherein component (a) 2% to 30% is present in an amount of by weight;
wherein component (c) 0% to 30% is present in an amount of by weight;
wherein component (d) 5% to 70% is present in an amount of by weight;
wherein component (e) 0 to 15% is present in an amount of by weight;
wherein component (f) is present in an amount of 0.05% to 5% by weight, and contains 0.1 to 10% by weight of silica based on the weight of polydimethylsiloxane;
wherein component (g) is present in an amount of 0 to 20% by weight; and
wherein component (h) is present in an amount of 5% to 85% by weight.
4. The herbicidal composition as claimed in claim 1;
wherein component (a) is present in an amount of 5% to 20% by weight;
wherein component (c) is present in an amount of 0% to 20% by weight;
wherein component (d) is present in an amount of 6% to 60% by weight;
wherein component (e) is present in an amount of 0 to 15% by weight;
wherein component (f) is present in an amount of 0.1% to 2% by weight, and contains 0.1 to 10% by weight of silica based on the weight of polydimethylsiloxane;
wherein component (g) is present in an amount of 0 to 15% by weight; and
wherein component (h) is present in an amount of 10% to 60% by weight.
5. The herbicidal composition as claimed in claim 1;
wherein the weight ratio of the water-soluble herbicidal active ingredients to the anionic surfactants, is in the range from 1:0.1 to 1:10.
6. The herbicidal composition as claimed in claim 2;
wherein the weight ratio of the water-soluble herbicidal active ingredients to the anionic surfactants, is in the range from 1:0.1 to 1:10.
7. The herbicidal composition as claimed in claim 2;
wherein the weight ratio of the water-soluble herbicidal active ingredients to the polydimethylsiloxane silica-containing defoamer is in the range from 1000:1 to 1:1.
8. The herbicidal composition as claimed in claim 3;
wherein the weight ratio of the water-soluble herbicidal active ingredients to the anionic surfactants, is in the range from 1:0.1 to 1:10.
9. The herbicidal composition as claimed in claim 4;
wherein the weight ratio of the water-soluble herbicidal active ingredients to the anionic surfactants, is in the range from 1:0.1 to 1:10.
10. The herbicidal composition as claimed in claim 1;
wherein the weight ratio of the anionic surfactants to the polydimethylsiloxane silica-containing defoamer is in the range from 2000:1 to 1:1.
11. The herbicidal composition as claimed in claim 2;
wherein the weight ratio of the anionic surfactants to the polydimethylsiloxane silica-containing defoamer is in the range from 2000:1 to 1:1.
12. The herbicidal composition as claimed in claim 3;
wherein the weight ratio of the anionic surfactants to the polydimethylsiloxane silica-containing defoamer is in the range from 2000:1 to 1:1.

13. The herbicidal composition as claimed in claim 5; wherein the weight ratio of the anionic surfactants to the polydimethylsiloxane silica-containing defoamer is in the range from 2000:1 to 1:1.

14. The herbicidal composition as claimed in claim 1; wherein the water-soluble herbicidal active ingredient is the herbicide glufosinate-ammonium.

15. The herbicidal composition as claimed in claim 13; wherein the water-soluble herbicidal active ingredient is the herbicide glufosinate-ammonium.

16. A process for preparing the herbicidal composition as defined in claim 1, comprising:

mixing components (a) and (c) to (g) present in the formulation with water (component (h)).

17. A method of controlling unwanted plant growth, comprising:

applying an effective amount of the herbicidal composition as claimed in claim 1 to the plants, to parts of plants, or to the area under cultivation.

\* \* \* \* \*